United States Patent
Fukata et al.

(10) Patent No.: US 6,645,515 B1
(45) Date of Patent: Nov. 11, 2003

(54) BACTERIOSTATIC COMPOSITION FOR SALMONELLAE

(75) Inventors: Tsuneo Fukata, Gifu (JP); Takao Ogawa, Ama-gun (JP); Kimio Hirose, Gifu (JP); Kyoji Kito, Nagoya (JP)

(73) Assignee: Meito Sangyo Kabushiki Kaisha, Aichi (JP)

( * ) Notice: Subject to any disclaimer, the term of this patent is extended or adjusted under 35 U.S.C. 154(b) by 0 days.

(21) Appl. No.: 09/856,826

(22) PCT Filed: Nov. 25, 1999

(86) PCT No.: PCT/JP99/06574

§ 371 (c)(1),
(2), (4) Date: May 25, 2001

(87) PCT Pub. No.: WO00/30661

PCT Pub. Date: Jun. 2, 2000

(30) Foreign Application Priority Data

Nov. 26, 1998 (JP) .............................. 10-335585

(51) Int. Cl.$^7$ ................................ A01N 25/34
(52) U.S. Cl. ............... 424/404; 424/405; 424/439; 424/442; 424/489; 424/234.1; 424/237.1; 424/246.1
(58) Field of Search ................. 424/404, 405, 424/234.1, 237.1, 246.1, 439, 442, 489

(56) References Cited

U.S. PATENT DOCUMENTS 4,399,221 A * 8/1983 Schneider et al. .......... 435/193
4,902,674 A 2/1990 Speights ...................... 514/23

FOREIGN PATENT DOCUMENTS

JP 409143083 A * 6/1997

OTHER PUBLICATIONS

Webster's New World Dictionary of American English, Third College Edition. Neufeldt and Guralnik Editors. Cleveland & New York. P. 1184.*

Ushijima, T. "Kenki renzoku baiyo ni okeru almonella typhimurium no zoshoku wo tsuyoku yokusei surunoni hitsuyona hitoni daichonai jozaikin to baichi seibun", Igaku to Seibutsugaku, vol. 120, No. 2, (1990), p. 75–79 (Chemical Abstracts, vol. 112, No. 213831 (1990)).

* cited by examiner

Primary Examiner—Thurman K. Page
Assistant Examiner—Liliana Di Nola-Baron
(74) Attorney, Agent, or Firm—Wenderoth, Lind & Ponack, L.L.P.

(57) ABSTRACT

Provided is a bacteriostatic composition for salmonellae containing, as the active ingredient, a fermented broth obtained by effecting fermentation with the use of a lactic acid bacteriium belonging to the genus Leuconostoc, Streptococcus or Streptobacterium in a sucrose-containing medium, or a preparation originating in the supernatant obtained by subjecting the fermented broth to fractional precipitation from a water-miscible organic solvent.

7 Claims, 1 Drawing Sheet

BACTERIOSTATIC COMPOSITION FOR SALMONELLAE

This application is a 371 application of PCT/JP99/06574 filed Nov. 25, 1999.

TECHNICAL FIELD

This invention relates to a bacteriostatic composition for salmonellae containing, as the active ingredient, a component originating in the fermented broth of a lactic acid bacterium. More specifically, the invention relates to a composition utilizable as a feed additive, or a medicine or a health food for prophylaxis or treatment a of salmonellosis.

BACKGROUND ART

Some of animals are infected with salmonella when they are infants shortly after their birth, or even after they have grown to adults, due to change of the environment, etc. For preventing this, prophylaxis by administration of antibiotics, vaccines, various viable cell agents [for example, a product obtained by growth of a strain belonging to the genus Streptococcus or Lactobacillus, competitive exclusion of salmonellae (CE agent)] or the like, mannose (a kind of sugar) aggregating pathogens and inhibiting their adhesion to the intestinal wall, or oligosaccharides, etc. as health food has been tried.

However, among these methods, antibiotics have the problems, for example that resistant strains are liable to occur, the normal bacterial flora advantageously acting on the living body is also excluded, and there is the possibility of movement and remaining of : the antibiotics in processed stock farm products ("Remaining of feed additives into stock farm products", Chikusan Handbook (Stock Raising Handbook), edited by Kentaro HIMENO et al., Kodansha Co., 1984, pp. 484–485).

Vaccines have the problems, for example that they are effective only on particular pathogens, and their effects last only for a limited period ("Nihon no Chikusangyo" (The Livestock Industry of Japan), The Latest Data Bank Predicting the Stock Raising of Japan, Chikusan Shuppan Co., 1989, pp. 21–35).

As to various viable cell agents, some of them need storage in a cool place, they are short in storage time and expensive, and it has been necessary to administer a large amount of a viable cell agent to animals having an established intestinal bacterial flora.

Mannan oligosaccharides aggregating pathogens and inhibiting their adhesion to the intestinal wall aggregate 48% of pathogenic salmonellae and inhibiting their adhesion to the intestinal wall, but are not effective on the residual pathogenic salmonellae, and has the problem [Mikio SHIMIZU, Characteristics and Usefulness of Mannan Oligosaccharides, "Yokei no Tomo" (Friend in chicken Raising), No. 6, 14–18 (1996)].

It is said that oligosaccharides promote the growth of bifid bacteria inhabiting the large intestine of animals and forming the intestinal bacterial flora together with other bacteria, and have a salmonellae-inhibiting effect, but they are expensive and, moreover, uncertain in the effect [for example, Tsuneo FUKADA et al., On salmonella infection-inhibiting effect of oligosaccharides in chickens, "Keibyo Kenpo" (Research Paper on Chicken Diseases) 31, 113–117 (1995)].

Further, these antibiotics, vaccines, various viable cell agents, and oligosaccharides such as mannan oligosaccharides aggregating pathogens and inhibiting their adhesion to the intestinal wall themselves do not contain any perfume components liked by animals, and some of them rather smell disliked by animals and are unfit as feed additives.

As stated above, prior art exerts certain action and effect on the object of salmonellae inhibition, but some of them give out a foul smell, and they themselves do not show an action to enhance animal's taste. Therefore, when they are used for example as feed additives, it has been difficult to increase the feed intake of animals and improve their physical condition.

Thus the object of the invention lies in providing a composition having a salmonella-inhibiting effect and, in addition, can increase animal's taste.

DISCLOSURE OF INVENTION

The present inventors have intensely studied for providing a composition capable of improving or obviating drawbacks following prior art, namely a composition which is effective for prophylaxis or treatment of salmonellae infection and can increase animal's taste. As a result, they found that a preparation originating in fermented broth with the use of a certain bacterium belonging to lactic acid bacteria can accomplish the object and completed the invention.

Thus according to the invention is provided a bacteriostatic composition for salmonellae containing, as the active ingredient, a preparation originating in a fermented broth obtained by effecting fermentation with the use of at least one strain belonging to lactic acid bacteria selected from the group consisting of the genera Leuconostoc, Streptococcus and Streptobacterium in a sucrose-containig nutrient medium.

Further, as another embodiment, there is provided a method for prophylaxis or treatment of salmonellosis comprising administering the preparation originating in the fermented broth to a test animal in an amount effective for prophylaxis or treatment of salmonellosis.

Still further, as another embodiment, there is also provided use of the preparation originating in the fermented broth as an active ingredient for preparing a composition for prophylaxis or treatment of salmonellosis of animals.

PREFERRED EMBODIMENTS FOR CARRYING OUT INVENTION

Figure 1:
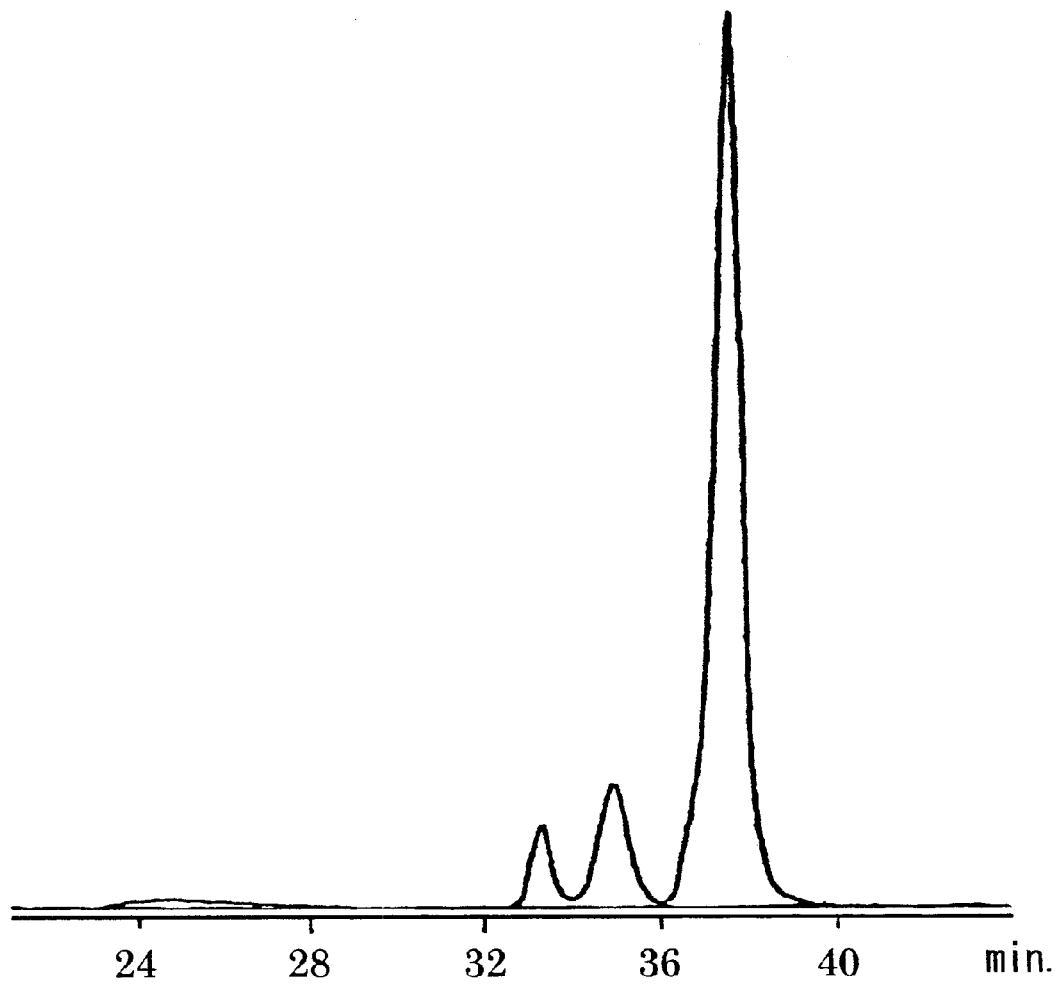
FIG. 1 is a chromatogram of the preparation according to the invention obtained in Example 1 which chromatogram was obtained under the described operation condition of liquid chromatography.

Lactic acid bacteria used in the fermentation according to the invention may be any bacteria belonging to the above genera, as long as they answer the object of the invention, and as specific ones, there can be mentioned *Leuconostoc mesenteroides, Leuconostoc dextranicum, Streptococcus bovis, Streptococcus mutans, Streptococcus sanguis* and *Streptobacterium dextranicum*. Preferred bacteria among them are *Leuconostoc mesenteroides* and *Streptococcus bovis*. Further as particularly preferred bacterium, there can be mentioned *Leuconostoc mesenteroides* used for production of dextran. As usable specific strains, there can, for example, be mentioned *Leuconostoc mesenteroides* ATCC 10830 (NRRL B-512), *Leuconostoc dextranicum* ATCC 19255 (NRRL B-3469), *Streptococcus bovis* ATCC 33317 (NCDO 597), *Streptococcus mutans* ATCC 25175 (NCTC 10449), *Streptococcus sanguis* ATCC 10556 and *Strepto-*

*bacterium dextranicum* ATCC 13134 (NRRL B-1254) available from American Type Culture Collection (ATCC). Further as to the above bacteria, when plural bacteria do not mutually influence badly their growth and physical functions, plural bacteria can be used together, but usually, it is suitable to use one bacterium.

The sucrose-containing nutrient medium for fermenting the bacterium contains, as a sucrose source, sucrose in an isolated form, or the squeezed residue of sugar-cane or sugar beet containing sucrose as a component, or molasses, beet pulp, bagasse or the like as a by-product formed when sugar is manufactured from sugar-cane or sugar beet. As components other than sucrose added to the medium, there can be mentioned substances or compounds substantially non-toxic on animals, for example, beer yeast extract, peptone, corn steep liquor, soybean protein, table salt, HCl, $K_2HPO_4$, etc.

The fermentation according to the invention can usually be carried out by sterilizing the medium, inoculating a suitable lactic acid bacterium, and conducting culture at around 25° C. under an anaerobic condition. The culture time is not limited since it varies depending on the bacterium used, temperature or medium composition, but it is at least needed to choose time of from the logarithmic phase to the stationary phase. The reason is that when the culture time is too short, there is a possibility that a composition having only a low salmonella effect on animals is brought about.

Thus, a fermented broth is obtained, and the bacteriostatic composition for salmonellae of the invention contains as the active ingredient the fermented broth itself or the supernatant itself obtained by subjecting the fermented broth, for example to fractional precipitation using a water-miscible organic solvent or a preparation originating in the supernatant. Thus, the preparation of the invention includes the fermented broth itself or a concentrate of the supernatant originating in the fermented broth, the later-described cell-free product, spray-dried product or freeze-dried product, etc. It is usually suitable to obtain the supernatant by fractional precipitation, and as the organic solvent used in the fractional precipitation, there can be mentioned ethanol, methanol, acetone, isopropyl alcohol etc. The amount of the used organic solvent based on the broth in the fractional precipitation treatment varies with respect to its optimum amount depending on the kind of the solvent used, but when ethanol is used, the organic solvent is usually used in an amount of 0.7 to 4 volume parts per 1 volume part of the broth. The treatment temperature is 15 to 35° C., preferably the ambient temperature.

A bacteriostatic composition for salmonellae containing a preparation obtained by removing the cells from the fermented broth, before or after the fractional precipitation treatment or simultaneously therewith is also provided by the invention. The removal of the cells can be carried out by filtration or centrifugation. The thus obtained preparation can conveniently used when utilized in medicine or health food, but also when used as a feed additive, the preparation is preferred in the point of easiness of use (for example, homogeneous compounding of the active ingredient is easy, etc.).

As understood from the above, the preparation originating in the supernatant used as the active ingredient in the composition of the invention can be used as the form of a purified concentrate obtained by concentrating a dextran fermentation by-product, which has been discarded or left without utilization as a by-product in the preparation of dextran, into 7 to 17-fold, as it is or if necessary after removing the cells, subjecting to desalting and removing the organic solvent. Thus, the preparation can be prepared extremely inexpensively. Such supernatant can be provided in a state of substantially not containing dextran depending on the kind or use amount of the organic solvent used, but such supernatant can also accomplish the desired object of the invention.

According to the invention is provided, for example, a liquid medicine obtained by merely dissolving the above preparation in a liquid or syrup (concentrate) state in water or physiological saline, or a composition obtained by compounding the preparation into pharmaceutical excipients or carriers, or raw materials for feed. There can also be provided as a solid composition obtained by compounding the liquid or syrup preparation into a granulating or solidifying agent commonly used in the pharmaceutical field or the feed field, for example granular glucose, silicic anhydride, cereal grain lees, bread crumbs, soybean cake, bran, cacao bean shells or the like. As to the solid composition, it is also possible to prepare the bacteriostatic composition for salmonellae of the invention in a solid state by freeze-drying or spray-drying the liquid or syrup preparation, or mixing the thus prepared dry matter with the above granulating agent or other excipients commonly used in the pharmaceutical or feed field. As the methods for the above preparation, compounding and mixing, methods therefor known per se can be used in accordance with the dosage forms.

In the invention it is surmised that the desired effect can be accomplished by the following action mechanism, although not limited thereto. When the lactic acid bacterium is inoculated into a sucrose-containing composition and cultured, glucose among glucose and fructose as the component sugars of sucrose polymerizes into dextran, and, on the other hand, fructose is produced, but in some occasion, the fructose exists in the form of oligo- or poly-fructose as a result of polymerization by the action of fructosyltransferase. In addition, various substances including lactic acid and perfume substances are produced from the bacterium, and therefore, a fermented broth comprising many components probably containing lactic acid, fructose, mannitol, leucrose, cells of the lactic acid bacterium used for the fermentation, and other components is formed. Since it is surmised that even after this fermented broth is subjected to the fractional precipitation treatment with the organic solvent as mentioned above, the supernatant fraction contains lactic acid, perfume components, fructose, mannitol, leucrose, dextran, oligo- or poly-fructose, and other culture broth components, and in some occasion, cels of the lactic acid bacterium used for the fermentation, the fermented broth can conveniently be used for providing the preparation of the invention. And it is surmised that by combination of these components, the preparation is harmless and enhances the taste of animals, and increases the physical condition of animals by its lowering effect of the pH of cecum dung, its inhibitory effect of invasion of the intestinal mucosa and its inhibitory effect of salmonella fixation in the salmonella attack test on chickens, and its action of inhibition of mortality and lowering of droppings pH, and exerts excellent effect in production of salmonellae-free hen's eggs, meat and cow's milk.

The use ratio of the preparation contained as the active ingredient in the bacteriostatic composition for salmonellae of the invention cannot be limited because the optimum amount is varied depending on its use object, for example, depending on use for medicine, health food or feed additives, but a person concerned will be able to determine it referring to the action and effect described in the later-described examples. Generally, when for example as a feed additive for formula feeds, a concentrate obtained by concentration of up to 12-fold is used, it can be incorporated so as to be 0.01 to 10.0% by weight, preferably 0.05 to 5.0% by weight based on the whole weight of the composition.

Such bacteriostatic composition for salmonellae can be utilized effectively for prophylaxis or treatment of salmonella infection or further for increase of feed take amount in poultry such as chickens and turkeys, livestock or pets such as cattle, horses, pigs, dogs and cats, and, in addition, humans.

The bacteriostatic composition for salmonellae of the invention is further specifically described bellow by examples, but the invention is not limited thereto.

EXAMPLE 1

Preparation of a Concentrate of the Supernatant in the Case Where Sucrose is Used as a Main Raw Material

*Leuconostoc mesenteroides* ATCC 10830 (NRRL B-512) as a lactic acid bacterium was inoculated into a medium of the following composition containing sucrose as a main raw material, and fermented at 25° C. for 24 hours under an anaerobic condition, and then 1 volume of ethanol was added to 1 volume of the fermented broth and the supernatant was collected. The supernatant was filtered to remove the cells, ethanol was distilled off at about 80° C. under reduced pressure (540–580 mmHg), and concentration was carried out so that the liquid amount got to be about 1/12 to prepare a concentrate of the supernatant. The properties and state and liquid chromatogram (see FIG. 1) of the concentrate prepared were as follows.

Composition of the Medium:

| | |
|---|---|
| Sucrose | 15.0% |
| Dipotassium hydrogenphosphate | 0.5% |
| Beer yeast extract | 0.2% |
| pH | 7.0 |

Properties and State of the Concentrate:

| | |
|---|---|
| Appearance | from light-brown to brown viscous liquid |
| Flavor | having sour-sweet flavor and free from nasty taste and nasty smell |
| Sugar content (Bx) | 65° |
| pH | 5.4 |
| Loss on drying | 31.6% |
| Fructose | 42.0% |
| Oligosaccharides* | 23.2% |

*From the result of FIG. 1, it is surmised that leucrose, mannitol, oligo- to poly-fructoses and dextran are contained.

Operation Condition of Liquid Chromatography (Corresponding to FIG. 1):

Sample amount: 80 µl of 2.0% by weight/volume solution
Column: G2000PW×2 (made by Toso Co.)
Eluent: 0.1M NaCl aqueous solution
Flow rate: 1.0 ml/min
Temperature: 25° C.
Pressure: 90 kg/cm$^2$
Detector: RI×1
Chart speed: 0.5 cm/min

EXAMPLE 2

Preparation of a Concentrate of the Supernatant in the Case Where Molasses is Used as a Main Raw Material

*Streptococcus bovis* ATCC 33317 (NCDO 597) as a lactic acid bacterium was inoculated into a medium of the following composition obtained by adding 2 volumes of distilled water to 1 volume of molasses, and fermented at 25° C. for 24 hours under an anaerobic condition, and then 1 volume of ethanol was added to 1 volume of the fermented broth and the supernatant was collected. The supernatant was filtered to remove the cells, ethanol was distilled off at about 80° C. underreduced pressure (540–580 mmHg), and concentration was carried out so that the liquid amount got to be about 1/12 to prepare a concentrate of the supernatant. The properties and state and the measured value by liquid chromatography of the concentrate prepared were as follows.

Composition of the Medium:

| | |
|---|---|
| Molasses | 15.0% |
| Dipotassium hydrogenphosphate | 0.1% |
| pH | 6.2 |

Properties and State of the Concentrate:

| | |
|---|---|
| Appearance | from light-brown to brown viscous liquid |
| Flavor | having sour-sweet flavor and free from nasty taste and nasty smell |
| Sugar content (Bx) | 62° |
| pH | 5.2 |
| Loss on drying | 33.5% |
| Fructose | 39.6% |
| Oligosaccharides | 22.9% |

EXAMPLE 3

Preparation of a Mixed Feed Using a Concentrate of a Supernatant as a Raw Material One kilogram of the concentrate prepared in Example 1 was added to 9 kg of granular glucose (Glufinal, made by Nihon Shiryo Kogyo Co.) as a powdering agent, and the mixture was sufficiently mixed in a horizontal paddle mixer for 5 minutes to prepare a mixed feed. The properties and state of the mixed feed prepared were as follows.

| | |
|---|---|
| Appearance | light-yellow powder |
| Flavor | having sour-sweet flavor and free from nasty taste and nasty smell |
| Loss on drying | 9.5% |
| Glucose | 79.0% |
| Fructose | 4.0% |
| Oligosaccharides | 2.5% |

EXAMPLE 4

Preparation of a Mixed Feed Using a Concentrate of a Supernatant as a Raw Material One kilogram of the concentrate prepared in Example 2 was added to 9 kg of silicic acid (made by Wako Junyaku Kogyo Co.) as an excipient for powdering, and the mixture was sufficiently mixed in a horizontal paddle mixer for 5 minutes to prepare a mixed feed. The properties and state of the mixed feed (also referred to as composition) prepared were as follows.

| | |
|---|---|
| Appearance | light-yellow powder |
| Flavor | having sour-sweet flavor and free from nasty taste and nasty smell |
| Loss on drying | 9.1% |
| Silicic acid | 80.5% |
| Fructose | 4.2% |
| Oligosaccharides | 2.8% |

EXAMPLE 5

Salmonella Fixation Inhibition Test on a Kind of Chicken from which Eggs are Taken Method: One-day-old white leghorns (♂) were divided into 3 groups, each group consisting of 30 chickens.

1) Control group: A group to which an experimental infant chick feed is given until the experiment is over.

2) Composition group: A group to which the feed to which 0.3% of the composition of Example 3 was added is given from the hatch date to the completion of the experiment 3) CE agent group: A group to which CE agent* in a viable cell agent was dissolved according to the explanatory leaflet, and 0.2 ml portions of the solution were compulsorily administered into the one-day-old chickens.
   * A feed obtained by culturing the contents of the cecum of a chicken About $10^7$ cells portions of *Salmonella enteritidis* (Phage type 4 type originating in *S. enteritidis* food poisoning) were orally administered to all the chickens at one-week-old. Autopsy was made on the next day, 1 week and 2 weeks after the *S. enteritidis* administration, and the *S. enteritidis* number per 1 g of the cecum contents was measured.

Result: *S. enteritidis* number per 1 g of the cecum contents (Table-1)

On the next day after the *S. enteritidis* administration, the *S. enteritidis* number in the composition group decreased by about 2 orders in comparison with the control group, but statistical significant difference was not seen.

On the 7th day after the *S. enteritidis* administration, the *S. enteritidis* number in the composition group significantly decreased in comparison with the control group.

On the 14th day after the *S. enteritidis* administration, the number of *S. enteritidis* separated was small in all the groups.

TABLE 1

*S. enteritidis* number per 1 g of the cecum contents in the case where *S. enteritidis* was administered to one-week-old chicks

| Treatment method | Days after the *S. enteritidis* administration | | |
|---|---|---|---|
| | 1 day | 7 days | 14 days |
| Control group | 5.20 ± 0.33[a] (10/10)[b] | 3.86 ± 0.68 (8/10) | 2.19 ± 0.91 (5/10) |
| Composition group | 3.53 ± 0.80 (9/10) | 1.42 ± 0.73* (3/10) | 0.49 ± 0.49 (1/10) |

TABLE 1-continued

*S. enteritidis* number per 1 g of the cecum contents in the case where *S. enteritidis* was administered to one-week-old chicks

| Treatment method | Days after the *S. enteritidis* administration | | |
|---|---|---|---|
| | 1 day | 7 days | 14 days |
| CE agent group | 4.63 ± 0.40 (10/10) | 3.69 ± 0.70 (8/10) | 1.55 ± 0.68 (4/10) |

*$P < 0.05$
[a] Average of logarithmic value of *S. enteritidis* number ± standard deviation
[b] Number of *S. enteritidis*-positive chickens/Number of chickens used
*There is a significant difference in 5% level of significance.

EXAMPLE 6

Salmonella Attack Test on Broilers

Method: One-day-old broilers (Arbor Acres) of 2 groups, each group consisting of 30 broilers, were prepared, and were divided into groups and treated as follows.

1) Control group: A group to which a broiler feed is given until the experiment was over.

2) Composition group: A group to which the broiler feed to which 0.3% of the composition of Example 3 was added is given until the experiment was over.

In both groups, the formula feed and water were freely given from one-day-old until 19-day-old. On the 13 days and 18 days, $10^8$ cells portions of *Salmonella enteritidis* were orally administered, and respectively on the next day, the broilers were dissected and the degree of intestinal mucosa invasion and the pH of the cecum dung were examined.

Results:
1) Invasion of intestinal mucosa (Table-2)

*S. enteritidis* attack in the 14-day-old was 26/30 broilers (86.6%) in the control group and 15/30 broilers (50%) in the composition group.

*S. enteritidis* attack the 19-day-old was 25/30 broilers (83.3%) in the control group and 16/30 broilers (53.3%) in the composition group.

In both 14-day-old and 19-day-old, the composition group significantly inhibited invasion of the intestinal mucosa by *S. enteritidis* in comparison with the control group.

2) pH of the cecum dung (Table-3)

In the attack of *S. enteritidis* in the 14-day-old, the pH was 6.5±0.3 in the control group and 5.6±0.2 in the composition group.

In the attack of *S. enteritidis* in the 19-day-old, the pH was 6.6±0.5 in the control group and 5.7±0.3 in the composition group.

In both 14-day-old and 19-day-old, the composition group significantly lowered the pH of the cecum contents in comparison with the control group.

TABLE 2

| Administration group | Attack bacterium | Invasion of intestinal mucosa | |
|---|---|---|---|
| | | 14-day-old | 19-day-old |
| Control group | *S. enteritidis* | 26/30 broilers (86.6%) | 25/30 broilers (83.3%) |
| Composition group | *S. enteritidis* | 15/30 broilers (50.0%) | 16/30 broilers (53.3%) |

*$P < 0.05$

TABLE 3 pH of cecum contents

| Administration group | Attack bacterium | 14-day-old | 19-day-old |
|---|---|---|---|
| Control group | S. enteritidis | 6.5 ± 0.3 | 6.6 ± 0.5 |
| Composition group | S. enteritidis | 5.6 ± 0.2* | 5.7 ± 0.3* |

*$P < 0.05$

EXAMPLE 7

Improvement Effect of Mortality in Salmonella Attack on Chickens

Method: Chickens weighing around 40 g of 3 groups, each group consisting of 45 chickens, were prepared, and were divided into groups and treated as follows.

1) Control group: A group to which a chicken feed is given until the experiment is over.

2) Composition group (0.1% addition): A group to which the chicken feed to which 0.1% of the composition of Example 3 was added is given until the experiment is over.

3) Composition group (0.3% addition): A group to which the chicken feed to which 0.3% of the composition of Example 3 was added is given until the experiment is over.

In all the three groups, 10 days after the initiation of the experiment, $2.7 \times 10^{11}$ CFU portions of *Salmonella enteritidis* were orally administered, and 2, 4 and 6 weeks thereafter, the number of salmonella cells in the droppings was measured.

Six weeks thereafter, the mortality and the pH of the droppings (6 chickens) were examined.

In all the three groups, for 6 weeks of from the initiation of the experiment to the completion thereof, the feed and water were freely given.

Results:

1) Number of salmonella cells in the droppings:

The number of salmonella cells in the droppings after 6 weeks was 0.95, 0.34 and 0.20×10 respectively after 2, 4 and 6 weeks of the control group, 0.6, 0.29 and 0.10×10 respectively after 2, 4 and 6 weeks of the composition group (0.1% addition), and 0.48, 0.21 and 0.00×10 respectively after 2, 4 and 6 weeks of the composition group (0.3% addition), and inhibition tendency was recognized.

2) Mortality:

The mortality after 6 weeks was 17.78% in the control group, 11.11% in the composition group (0.1% addition), and 6.67% in the composition group (0.3% addition), and inhibition tendency was recognized.

3) Droppings pH

Droppings pH after 6 weeks was 7.17 in the control group, 6.22 in the composition group (0.1% addition), and 6.05 in the composition group (0.3% addition), and significant difference was recognized.

TABLE 4

Number of Salmonella cells, mortality and droppings pH

| Treatment method | Salmonella cells number | | | Mortality (%) | Droppings pH |
|---|---|---|---|---|---|
| | after 2 weeks | after 4 weeks | after 6 weeks | | |
| Control group | 0.95 | 0.34 | 0.20 | 17.78 | 7.17 |
| Composition group (0.1% addition) | 0.60 | 0.29 | 0.10 | 11.11 | 6.22* |
| Composition group (0.3% addition) | 0.48 | 0.21 | 0.00 | 6.67 | 6.05* |

*There is a significant difference

EXAMPLE 8

Improving Effect of Mortality in Heat Stress

Method: Chickens weighing around 40 g of 3 groups, each group consisting of 45 chickens, were prepared, and were divided into groups and treated as follows.

1) Control group: A group to which a chicken feed is given until the experiment is over.

2) Composition group (0.1% addition): A group to which the chicken feed to which 0.1% of the composition of Example 3 was added is given until the experiment is over.

3) Composition group (0.3% addition): A group to which the chicken feed to which. 0.3% of the composition of Example 3 was added is given until the experiment is over.

In all the three groups, for 6 weeks of from the initiation of the experiment to the completion thereof, the chickens were raised at a temperature of 40±1° C. and at a humidity of 75±5% for 12 hours of one day, and at 24–26° C. for the remaining 12 hours.

In all the three groups, for 6 weeks of from the initiation of the experiment to the completion thereof, the feed and water were freely given.

Six weeks thereafter, the mortality and the pH of the droppings (6 chickens) were examined (Table-5).

Results:

1) Mortality:

The mortality after 6 weeks was 33.33% in the control group, 17.78% in the composition group (0.1% addition), and 11.11% in the composition group (0.3% addition), and inhibition tendency was recognized.

2) Droppings pH

Droppings pH after 6 weeks was 7.12 in the control group, 6.28 in the composition group (0.1% addition), and 6.23 in the composition group (0.3% addition), and significant difference was recognized.

TABLE 5

Mortality and droppings pH

| Treatment method | Mortality (%) | Droppings pH |
|---|---|---|
| Control group | 33.33 | 7.12 |
| Composition group (0.1% addition) | 17.78 | 6.28* |
| Composition group (0.3% addition) | 11.11 | 6.23* |

*There is a significant difference

Industrial Applicability

According to the invention, when the preparation is added in an amount of 0.01 to 10%, preferably 0.05 to 5.0% to a formula feed for animals as infants shortly after their birth or adults, and the mixture is orally administered to an animal salmonella infection in the cecum dung and invasion of the intestinal mucosa are prevented and treated, and production of salmonella-free stock farm products is made possible. Therefore, the invention can, for example, be utilized in the poultry industry.

What is claimed is:

1. A method for treating salmonellosis of poultry or livestock which comprises administering, to an animal of poultry or livestock, a pharmaceutically effective amount of a dextran fermentation by-product obtained by effecting fermentation with the use of at least one strain belonging to lactic acid bacteria which is selected from the group consisting of the genera Leuconostoc, Streptococcus and Streptobacterium in a sucrose-containing nutrient medium.

2. The method according to claim 1, wherein the lactic acid bacterium of the genus Leuconostoc is *Leuconostoc mesenteroides*.

3. The method according to claim 1, wherein the lactic acid bacterium of the genus Streptococcus is *Streptococcus bovis*.

4. The method according to claim 1, wherein the dextran fermentation by-product is combined with a granulating agent.

5. The method according to claim 1, wherein the dextran fermentation by-product is administered as a composition which comprises the dextran fermentation by-product in combination with a pharmaceutical excipient or carrier.

6. The method according to claim 1, wherein the dextran fermentation by-product is administered as a composition which comprises the dextran fermentation by-product in combination with a raw material for feed.

7. The method according to claim 6, wherein the content of the dextran fermentation by-product in the composition is at least 0.1% by weight based on the total weight of the composition.

* * * * *